United States Patent
Wehner et al.

(10) Patent No.: US 6,174,941 B1
(45) Date of Patent: Jan. 16, 2001

(54) NH$_2$-MODIFIED 6-AMINOURACILS AS STABILIZERS FOR HALOGENATED POLYMERS

(75) Inventors: Wolfgang Wehner, Zwingenberg; Hans-Helmut Friedrich, Lautertal-Gadernheim; Rolf Drewes, Neuenburg, all of (DE)

(73) Assignee: Witco Vinyl Additives GmbH, Lampertheim (DE)

(*) Notice: Under 35 U.S.C. 154(b), the term of this patent shall be extended for 0 days.

(21) Appl. No.: 09/336,079

(22) Filed: Jun. 18, 1999

(30) Foreign Application Priority Data

Jun. 26, 1998 (CH) .................................................... 1370/98

(51) Int. Cl.$^7$ ................................ C08K 5/34; C08K 5/15; C08K 5/04; C08K 3/10; C08K 3/30

(52) U.S. Cl. .......................... 524/100; 524/114; 524/399; 524/400; 524/413; 524/423; 524/430; 524/450; 524/56; 544/312

(58) Field of Search ............................... 544/312; 524/56, 524/100, 114, 399, 400, 413, 423, 430, 434, 450

(56) References Cited

U.S. PATENT DOCUMENTS

| | | |
|---|---|---|
| 2,598,936 | 6/1952 | Papesch et al. . |
| 2,950,952 | 8/1960 | Breck et al. . |
| 3,243,394 | 3/1966 | Dietz et al. . |
| 3,436,362 | 4/1969 | Hayer et al. . |
| 4,000,100 | 12/1976 | Baldyga . |
| 4,060,512 | 11/1977 | Scheidl et al. . |
| 4,197,209 | 4/1980 | Zinke et al. . |
| 4,333,859 | 6/1982 | Vaughan et al. . |
| 4,339,383 | 7/1982 | Wehner et al. . |
| 4,352,903 | 10/1982 | Abeler . |
| 4,503,023 | 3/1985 | Breck et al. . |
| 4,590,233 | 5/1986 | Erwied et al. . |
| 4,639,482 | 1/1987 | Müller et al. . |
| 4,656,209 | 4/1987 | Wehner et al. . |
| 4,743,640 | 5/1988 | Wirth et al. . |
| 4,992,504 | 2/1991 | Wirth et al. . |
| 5,030,671 | 7/1991 | Wehner et al. . |
| 5,071,898 | 12/1991 | Wirth et al. . |
| 5,177,135 | 1/1993 | Wehner et al. . |
| 5,322,907 | 6/1994 | Cotting et al. . |
| 5,516,827 | 5/1996 | Kaufhold et al. . |

FOREIGN PATENT DOCUMENTS

| | | |
|---|---|---|
| 38 43 581 A1 | 7/1989 | (DE) . |
| 40 31 818 A1 | 4/1992 | (DE) . |
| 42 04 887 A1 | 8/1993 | (DE) . |
| 0 090 748 B1 | 10/1983 | (EP) . |
| 0 108 023 B1 | 5/1984 | (EP) . |
| 0 225 261 A1 | 6/1987 | (EP) . |
| 0 259 783 B1 | 3/1988 | (EP) . |
| 0 384 070 A2 | 8/1990 | (EP) . |
| 0 394 547 A2 | 10/1990 | (EP) . |
| 0 400 961 A2 | 12/1990 | (EP) . |
| 0 457 471 A2 | 11/1991 | (EP) . |
| 0 768 336 A2 | 4/1997 | (EP) . |
| 2 459 816 | 6/1979 | (FR) . |
| 2 552 440 | 9/1983 | (FR) . |
| 841812 | 7/1960 | (GB) . |
| WO 93/20135 | 10/1993 | (WO) . |
| WO 94/24200 | 10/1994 | (WO) . |
| WO 94/26662 | 11/1994 | (WO) . |
| WO 96/04280 | 2/1996 | (WO) . |

Primary Examiner—Kriellion Sanders
(74) Attorney, Agent, or Firm—Scully, Scott, Murphy & Presser

(57) ABSTRACT

A description is given of compounds of the general formula I

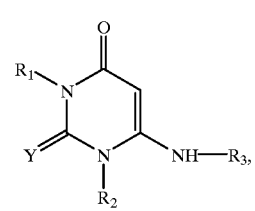

where

Y is oxygen or sulfur, and

R$_1$ and R$_2$ independently of one another are C$_1$–C$_{18}$-alkyl, C$_3$–C$_6$-alkenyl, unsubstituted or C$_1$–C$_4$-alkoxy-, C$_5$–C$_8$-cycloalkyl-, —OH— and/or Cl-substituted C$_1$–C$_{18}$-alkyl, C$_5$–C$_8$-cycloalkyl, phenyl or C$_7$–C$_9$-phenylalkyl which is unsubstituted or substituted on the phenyl ring by C$_1$–C$_4$-alkyl, C$_1$–C$_4$-alkoxy, C$_5$–C$_8$-cycloalkyl, —OH and/or Cl, and R$_3$ is unsubstituted C$_9$–C$_{18}$-alkyl or is C$_1$–C$_{18}$-alkyl substituted by —OH, C$_1$–C$_{12}$-alkoxy, phenoxy, C$_6$–C$_8$-alkylphenoxy, C$_7$–C$_9$-alkoxyphenyl, —C=O(OR$_4$) and/or —O—COR$_4$, or is C$_3$–C$_6$-alkenyl, C$_5$–C$_8$-cycloalkyl, or mono- to tri-OH—, —C$_1$–C$_4$-alkyl-, —C$_1$–C$_4$-alkoxy-, —C=O(OR$_4$)— and/or —O—COR$_4$-substituted phenyl or naphthyl, and where R$_4$ is C$_1$–C$_{12}$-alkyl, which are suitable for stabilizing chlorine-containing polymers, especially PVC.

24 Claims, No Drawings

$NH_2$-MODIFIED 6-AMINOURACILS AS STABILIZERS FOR HALOGENATED POLYMERS

BACKGROUND OF THE INVENTION

1. Technical Field

The invention relates to 1,3-disubstituted 6-aminouracils which are of the formula I depicted below and are intended for stabilizing chlorine-containing polymers, especially PVC.

2. Prior Art

PVC can be stabilized by a range of additives. Compounds of lead, of barium and of cadmium are particularly suitable for this purpose but are nowadays controversial on ecological grounds or because of their heavy metal content (cf. "Kunststoffadditive", R. Gächter/H. Müller, Carl Hanser Verlag, 3rd ed., 1989, pages 303–311, and "Kunststoff Handbuch PVC", volume 2/1, W. Becker/D. Braun, Carl Hanser Verlag, 2nd ed., 1985, pages 531–538; and also Kirk-Othmer: "Encyclopedia of Chemical Technology", $4^{th}$ ed., 1994, Vol. 12, Heat Stabilizers, pp. 1071–1091). The search therefore continues for effective stabilizers and stabilizer combinations which are free from lead, barium and cadmium.

1,3-disubstituted aminouracils have already been described in U.S. Pat. No. 3,436,362, U.S. Pat. No. 4,656,209, U.S. Pat. No. 4,352,903 and EP-A-0 768 336 and can be prepared by known methods in one (or more) process steps.

SUMMARY OF THE INVENTION

It has now been found that the 1,3-disubstituted 6-aminoruacils of the general formula I

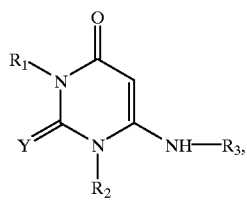

(I)

where

Y is oxygen or sulfur, and $R_1$ and $R_2$ independently of one another are $C_1$–$C_{18}$-alkyl, $C_3$–$C_6$-alkenyl, unsubstituted or $C_1$–$C_4$-alkoxy-, $C_5$–$C_8$-cycloalkyl-, —OH— and/or Cl-substituted $C_1$–$C_{18}$-alkyl, $C_5$–$C_8$-cycloalkyl, phenyl or $C_7$–$C_9$-phenylalkyl which is unsubstituted or substituted on the phenyl ring by $C_1$–$C_4$-alkyl, $C_1$–$C_4$-alkoxy, $C_5$–$C_8$-cycloalkyl, —OH and /or Cl, and $R_3$ is unsubstituted $C_9$–$C_{18}$-alkyl or is $C_1$–$C_{18}$-alkyl substituted up to 5 times by —OH, $C_1$–$C_{12}$-alkoxy, phenoxy, $C_6$–$C_8$-alkylphenoxy, $C_7$–$C_9$-alkoxyphenyl, —C=O($OR_4$) and/or —O—$COR_4$, or is $C_3$–$C_6$-alkenyl, $C_5$–$C_8$-cycloalkyl, or mono- to tri-OH—, —$C_1$–$C_4$-alkyl-, —$C_1$–$C_4$-alkoxy-, —C=O($OR_4$)— and/or —O—$COR_4$-substituted phenyl or naphthyl, and where $R_4$ is $C_1$–$C_{12}$-alkyl, are particularly suitable for stabilizing chlorine-containing polymers such as PVC, for example.

For compounds of the formula I, $C_1$–$C_4$-alkyl is, for example, methyl, ethyl, n-propyl, isopropyl, n-, i-, sec- or t-butyl.

$C_5$–$C_{18}$-alkyl is, for example, pentyl, hexyl, heptyl, octyl, 2-ethylhexyl, i-octyl, decyl, nonyl, undecyl, dodecyl, pentadecyl, hexadecyl, etc.

Preference is given to methyl, ethyl, propyl and butyl, especially methyl.

$C_1$–$C_{12}$-Alkoxy is, for example, methoxy, ethoxy, propoxy, n-, i- and tert-butoxy, n-, i-, tert- and neo-pentoxy, hexoxy etc.

Methoxy and ethoxy are preferred.

$C_6$–$C_8$-Alkylphenoxy is, for example, methylphenoxy, dimethylphenoxy or ethylphenoxy.

$C_7$–$C_9$-Alkoxyphenyl is, for example, methoxyphenyl, dimethoxyphenyl, trimethoxypenyl, ethoxyphenyl, propoxyphenyl, etc.

$C_3$–$C_6$-alkenyl is allyl, 1-butenyl, 2-butenyl, 3-butenyl, isobutenyl, 1-pentenyl, 2-pentenyl, 3-pentenyl, 4-pentenyl, 1-hexenyl, 2-hexenyl, 3-hexenyl, 4-hexenyl, 5-hexenyl and their isomers. Preference is given to allyl.

$C_5$–$C_8$-cycloalkyl is, for example, cyclopentyl, cyclohexyl, cycloheptyl or cyclooctyl, preferably cyclohexyl.

$C_7$–$C_{10}$-phenylalkyl is, for example, benzyl, 1- or 2-phenylethyl, 3-phenylpropyl, α,α-dimethylbenzyl or 2-phenylisopropyl, preferably benzyl and 2-phenethyl, especially benzyl.

If the aromatic radical is substituted then it is preferably substituted by three, two or, in particular, one substituent and the substituents are, in particular, hydroxyl, methyl, ethyl, tert-butyl, methoxy or ethoxy.

Preference is given to compounds of the formula I in which Y is oxygen and to those in which the radicals $R_1$ and $R_2$ independently of one another are $C_1$–$C_8$-alkyl, allyl or $C_7$–$C_9$-phenylalkyl.

Further advantageous compounds are those in which Y is sulfur.

Preference is also given to compounds of the formula I in which $R_3$ is $C_9$–$C_{18}$-alkyl or —OH-substituted $C_1$–$C_{12}$-alkyl, cyclohexyl, allyl, $C_7$–$C_9$-phenylalkyl, or —OH—, $C_1$–$C_4$-alkyl-, $C_1$–$C_4$-alkoxy-, —C=O($OR_4$)— and/or —O—$COR_4$-substituted phenyl or naphthyl. Very particular preference is given to compounds of the formula I in which $R_1$ and $R_2$ are $C_1$–$C_4$-alkyl and $R_3$ is —OH-substituted $C_1$–$C_4$-alkyl, benzyl, phenyl, —OH-substituted phenyl, or phenyl which is substituted by —OH and from 1 to 3 times by $C_1$–$C_4$-alkyl.

In order to achieve stabilization in the chlorine-containing polymer, the compounds of the formula I are to be used in a proportion of judiciously from 0.01 to 10% by weight, preferably from 0.05 to 5% by weight and, in particular, from 0.1 to 3% by weight.

It is also possible to employ combinations of compounds of the general formula I with other customary additives and stabilizers, for example with polyols and disaccharide alcohols and/or perchlorate compounds and/or glycidyl compounds and/or zeolite compounds and/or layered lattice compounds (hydrotalcites) and also, for example, light stabilizers. Examples of such additional components are listed and elucidated below.

DETAILED DESCRIPTION OF THE INVENTION

Polyols and Disaccharide Alcohols

Examples of suitable compounds of this type are:

pentaerythritol, dipentaerythritol, tripentaerythritol, trimethylolethane, bistrimethylolpropane, inositol (cyclitols), polyvinyl alcohol, bis-trimethylolethane, trimethylolpropane, sorbitol (hexitols), maltitol, isomaltitol, cellobiitol, lactitol, lycasine, mannitol, lactose, leucrose, tris(hydroxyethyl) isocyanurate, tris (hydroxypropyl) isocyanurate, palatinitol, tetramethylolcyclohexanol, tetramethylolcyclopentanol, tetramethylolcyclopyranol, xylitol, arabinitol (pentitols), tetritols, glycerol, diglycerol, polyglycerol, thiodiglycerol or 1-O-α-D-glycopyranosyl-D-mannitol dihydrate.

Of these, preference is given to the disaccharide alcohols.

It is also possible to use polyol syrups, such as sorbitol, mannitol and maltitol syrup. The polyols can be employed in an amount of, for example, from 0.01 to 20, judiciously from 0.1 to 20 and, in particular, from 0.1 to 10 parts by weight per 100 parts by weight of PVC.

Perchlorate Compounds

Examples are those of the formula $M(ClO_4)_n$, in which M is Li, Na, K, Mg, Ca, Sr, Ba, Zn, Al, La or Ce. Depending on the valency of M, the index n is 1, 2 or 3. The perchlorate salts can be present as solutions or can have been complexed with alcohols (polyols, cyclodextrins) or ether alcohols or ester alcohols. The ester alcohols also include the polyol partial esters. In the case of polyhydric alcohols or polyols, their dimers, trimers, oligomers and polymers are also suitable, such as di-, tri-, tetra- and polyglycols and also di-, tri- and tetrapentaerythritol or polyvinyl alcohol in various degrees of polymerization.

Other suitable solvents are phosphate esters and also cyclic and acyclic carbonates.

In this context, the perchlorate salts can be employed in various common forms of presentation; for example, as a salt or solution in water or an organic solvent as such, or adsorbed on a support material such as PVC, Ca silicate, zeolites or hydrotalcites, or bound by chemical reaction into a hydrotalcite or into another layered lattice compound. As polyol partial ethers, preference is given to glycerol monoethers and glycerol monothioethers.

Further embodiments are described in EP 0 394 547, EP 0 457 471 and WO 94/24200.

The perchlorates can be employed in an amount of, for example, from 0.001 to 5, judiciously from 0.01 to 3, and, with particular preference, from 0.01 to 2 parts by weight per 100 parts by weight of PVC.

Glycidyl Compounds

These contain the glycidyl group

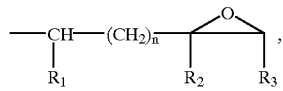

attached directly to carbon, oxygen, nitrogen or sulfur atoms, and in such compounds $R_1$ and $R_3$ are either both hydrogen and $R_2$ is hydrogen or methyl and n is 0 or $R_1$ and $R_3$ together are $—CH_2—CH_2—$ or $—CH_2—CH_2—CH_2—$ and in that case $R_2$ is hydrogen and n is 0 or 1.

I) Glycidyl esters and β-methylglycidyl esters obtainable by reacting a compound having at least one carboxyl group in the molecule with epichlorohydrin or glyceroldichlorohydrin or β-methylepichlorohydrin. The reaction takes place judiciously in the presence of bases.

As compounds having at least one carboxyl group in the molecule it is possible to use aliphatic carboxylic acids. Examples of these carboxylic acids are glutaric, adipic, pimelic, suberic, azelaic and sebacic acid or dimerized or trimerized linoleic acid, acrylic and methacrylic acid, caproic, caprylic, lauric, myristic, palmitic, stearic and pelargonic acid, and also the acids mentioned in connection with the organozinc compounds.

However, it is also possible to employ cycloaliphatic carboxylic acids, such as, for example, cyclohexanecarboxylic, tetrahydrophthalic, 4-methyltetrahydrophthalic, hexahydrophthalic or 4-methylhexahydrophthalic acid.

Aromatic carboxylic acids can also be used, examples being benzoic, phthalic, isophthalic, trimellitic and pyromellitic acid.

It is likewise possible to make use of carboxyl-terminated adducts of, for example, trimellitic acid with polyols, such as glycerol or 2,2-bis(4-hydroxycyclohexyl)propane. Other epoxide compounds which can be used in the context of this invention are given in EP 0 506 617.

II) Glycidyl ethers or β-methylglycidyl ethers obtainable by reacting a compound having at least one free alcoholic hydroxyl group and/or phenolic hydroxyl group with an appropriately substituted epichlorohydrin under alkaline conditions or in the presence of an acidic catalyst with subsequent alkali treatment.

Ethers of this type are derived, for example, from acyclic alcohols, such as ethylene glycol, diethylene glycol and higher poly(oxyethylene) glycols, propane-1,2-diol, or poly (oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, bistri-methylolpropane, pentaerythritol, sorbitol, and from polyepichlorohydrins, butanol, amyl alcohol, pentanol, and from monofunctional alcohols such as isooctanol, 2-ethylhexanol, isodecanol and also $C_7$–$C_9$-alkanol and $C_9$–$C_{11}$-alkanol mixtures. They are also derived, however, for example, from cycloaliphatic alcohols, such as 1,3- or 1,4-dihydroxycyclohexane, bis(4-hydroxycyclohexyl)methane, 2,2-bis-(4-hydroxycyclohexyl)propane or 1,1-bis(hydroxymethyl) cyclohex-3-ene, or they possess aromatic nuclei, such as N,N-bis(2-hydroxyethyl)aniline or p,p'-bis(2-hydroxyethylamino)diphenylmethane.

The epoxide compounds can also be derived from mononuclear phenols, such as, for example, from phenol, resorcinol or hydroquinone; or, they are based on polynuclear phenols, such as, for example, on bis(4-hydroxyphenyl) methane, 2,2-bis(4-hydroxyphenyl)propane, 2,2-bis(3,5-dibromo-4-hydroxyphenyl)-propane, on 4,4'-dihydroxydiphenyl sulfone or on condensates of phenols with formaldehyde obtained under acidic conditions, such as phenol novolaks.

Examples of further possible terminal epoxides are: glycidyl 1-naphthyl ether, glycidyl 2-phenylphenyl ether, 2-biphenylyl glycidyl ether, N-(2,3-epoxypropyl) phthalimide and 2,3-epoxypropyl 4-methoxyphenyl ether.

III) N-Glycidyl compounds obtainable by dehydrochlorination of the reaction products of epichlorohydrin with amines containing at least one amino hydrogen atom. These amines are, for example, aniline, N-methylaniline, toluidine, n-butylamine, bis(4-aminophenyl)methane, m-xylylenediamine or bis(4-methylaminophenyl)methane, and also N,N,O-triglycidyl-m-aminophenol or N,N,O-triglycidyl-p-aminophenol.

However, the N-glycidyl compounds also include N,N'-di, N,N',N''-tri- and N,N',N'',N'''-tetraglycidyl derivatives of cycloalkyleneureas, such as ethyleneurea or 1,3-propyleneurea and N,N'-diglycidyl derivatives of hydantoins, such as of 5,5-dimethylhydantoin or glycoluril and triglycidyl isocyanurate.

IV) S-Glycidyl compounds such as di-S-glycidyl derivatives derived from dithiols, such as ethane-1,2-dithiol or bis(4-mercaptomethylphenyl) ether, for example.

V) Epoxy compounds having a radical of the above formula in which $R_1$ and $R_3$ together are —$CH_2$—$CH_2$— and n is 0 are bis(2,3-epoxycyclopentyl) ether, 2,3-epoxycyclopentylglycidyl ether or 1,2-bis(2,3-epoxycyclopentyloxy) ethane. An epoxy resin having a radical of the above formula in which $R_1$ and $R_3$ together are —$CH_2$—$CH_2$— and n is 1 is, for example, (3',4'-epoxy-6'-methylcyclohexyl)methyl 3,4-epoxy-6-methylcyclohexanecarboxylate.

Examples of suitable terminal epoxides are:
a) liquid bisphenol A diglycidyl ethers, such as Araldit®GY 240, Araldit®GY 250, Araldit®GY 260, Araldit®GY 266, Araldit®GY 2600, Araldit®MY 790;
b) solid bisphenol A diglycidyl ethers, such as Araldit®GT 6071, Araldit®GT 7071, Araldit®GT 7072, Araldit®GT 6063, Araldit®GT 7203, Araldit®GT 6064, Araldit®GT 7304, Araldit®GT 7004, Araldit®GT 6084, Araldit®GT 1999, Araldit®GT 7077, Araldit®GT 6097, Araldit®GT 7097, Araldit®GT 7008, Araldit®GT 6099, Araldit®GT 6608, Araldit®GT 6609, Araldit®GT 6610;
c) liquid bisphenol F diglycidyl ethers, such as Araldit®GY 281, Araldit®PY 302, Araldit®PY 306;
d) solid polyglycidyl ethers of tetraphenylethane, such as CG Epoxy Resin®0163;
e) solid and liquid polyglycidyl ethers of phenol-formaldehyde novolak, such as EPN 1138, EPN 1139, GY 1180, PY 307;
f) solid and liquid polyglycidyl ethers of o-cresol-formaldehyde novolak, such as ECN 1235, ECN 1273, ECN 1280, ECN 1299;
g) liquid glycidyl ethers of alcohols, such as Shell® Glycidyl ether 162, Araldit®DY 0390, Araldit®DY 0391;
h) liquid glycidyl ethers of carboxylic acids, such as Shell®Cardura E terephthalic acid ester, trimellitic acid ester, Araldit®PY 284;
i) solid heterocyclic epoxy resins (triglycidyl isocyanurate), such as Araldit®PT 810;
j) liquid cycloaliphatic epoxy resins such as Araldit®CY 179;
k) liquid N,N,O-triglycidyl ethers of p-aminophenol, such as Araldit®MY 0510;
l) tetraglycidyl-4,4'-methylenebenzamine or N,N,N',N'-tetraglycidyldiamino-phenylmethane, such as Araldit®MY 720, Araldit®MY 721.

Preference is given to the use of epoxy compounds having two functional groups. In principle, however, it is also possible to employ epoxy compounds having one, three or more functional groups.

Use is made predominantly of epoxy compounds, especially diglycidyl compounds, having aromatic groups.

If desired, it is also possible to employ a mixture of different epoxy compounds. Particular preference is given as terminal epoxy compounds to diglycidyl ethers based on bisphenols, such as on 2,2-bis(4-hydroxyphenyl)propane (bisphenol A), bis(4-hydroxyphenyl)methane or mixtures of bis(ortho/para-hydroxyphenyl)methane (bisphenol F), for example.

The terminal epoxy compounds can be employed in an amount of preferably at least 0.1 part, for example from 0.1 to 50, judiciously from 1 to 30 and in particular, from 1 to 25 parts by weight, per 100 parts by weight of PVC.

Hydrotalcites

The chemical composition of these compounds is known to the person skilled in the art, for example, from patents DE 3 843 581, U.S. Pat. No. 4,000,100, EP 0 062 813 and WO 93/20135.

Compounds from the series of the hydrotalcites can be described by the following general formula

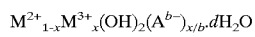

where
$M^{2+}$=one or more metals from the group Mg, Ca, Sr, Zn and Sn,
$M^{3+}$=Al, or B,
$A^n$ is an anion having the valency n,
b is a number from 1–2,
0<x<0.5,
m is a number from 0–20.
Preferably
$A^n$=$OH^-$, $ClO_4^-$, $HCO_3^-$, $CH_3COO^-$, $C_6H_5COO^-$, $CO_3^{2-}$, $(CHOHCOO)_2^{2-}$, $(CH_2COO)_2^{2-}$, $CH_3CHOHCOO^-$, $HPO_3^-$ or $HPO_4^{2-}$;
Examples of hydrotalcites are
$Al_2O_3 \cdot 6MgO \cdot CO_2 \cdot 12H_2O$ (i), $Mg_{4.5}Al_2(OH)_{13} \cdot CO_3 \cdot 3.5H_2O$ (ii), $4MgO \cdot Al_2O_3 \cdot CO_2 \cdot 9H_2O$ (iii), $4MgO \cdot Al_2O_3 \cdot CO_2 \cdot 6H_2O$,
$ZnO \cdot 3MgO \cdot Al_2O_3 \cdot CO_2 \cdot 8-9H_2O$ and $ZnO \cdot 3MgO \cdot Al_2O_3 \cdot CO_2 \cdot 5-6H_2O$.
Very particular preference is given to types i, ii and iii.

Zeolites (Alkali Metal and Alkaline Earth Metal Alumosilicates)

These can be described by the following general formula

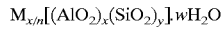

in which n is the charge of the cation M;
M is an element from the first or second main group, such as Li, Na, K, Mg, Ca, Sr or Ba;
y:x is a number from 0.8 to 15, preferably from 0.8 to 1.2; and
w is a number from 0 to 300, preferably from 0.5 to 30.

Examples of zeolites are sodium aluminosilicates of the formulae
$Na_{12}Al_{12}Si_{12}O_{48} \cdot 27H_2O$ [zeolite A], $Na_6Al_6Si_6O_{24} \cdot 2NaX \cdot 7.5H_2O$, X=OH, halogen, $ClO_4$ [sodalite]; $Na_6Al_6Si_{30}O_{72} \cdot 24H_2O$; $Na_8Al_8Si_{40}O_{96} \cdot 24H_2O$; $Na_{16}Al_{16}Si_{24}O_{80} \cdot 16H_2O$; $Na_{16}Al_{16}Si_{32}O_{96} \cdot 16H_2O$; $Na_{56}Al_{56}Si_{136}O_{384} \cdot 250H_2O$ [zeolite Y], $Na_{86}Al_{86}Si_{106}O_{384} \cdot 264H_2O$ [zeolite X]; or the zeolites preparable by complete or partial replacement of the Na atoms by Li, K, Mg, Ca, Sr or Zn atoms, such as $(Na,K)_{10}Al_{10}Si_{22}O_{64} \cdot 20H_2O$; $Ca_{4.5}Na_3[(AlO_2)_{12}(SiO_2)_{12}] \cdot 30H_2O$; $K_9Na_3[(AlO_2)_{12}(SiO_2)_{12}] \cdot 27H_2O$, Preferred zeolites are those of the formulae $Na_{12}Al_{12}Si_{12}O_{48} \cdot 27H_2O$ [zeolite A], $Na_6Al_6Si_6O_{24} \cdot 2NaX \cdot 7.5H_2O$, X=OH, Cl, $ClO_4$, $1/2CO_3$ [sodalite]

$Na_6Al_6Si_{30}O_{72} \cdot 24 H_2O$, $Na_8Al_8Si_{40}O_{96} \cdot 24 H_2O$, $Na_{16}Al_{16}Si_{24}O_{80} \cdot 16 H_2O$, $Na_{16}Al_{16}Si_{32}O_{969} \cdot 16 H_2O$, $Na_{56}Al_{56}Si_{136}O_{384} \cdot 250 H_2O$ [zeolite Y], $Na_{86}Al_{86}Si_{106}O_{384} \cdot 264 H_2O$ [zeolite X]

and those X and Y zeolites having an Al/Si ratio of about 1:1, or the zeolites preparable by complete or partial replacement of the Na atoms by Li, K, Mg, Ca, Sr, Ba or Zn atoms, such as $(Na,K)_{10}Al_{10}Si_{22}O_{64} \cdot 20 H_2O$ $Ca_{4.5}Na_3[(AlO_2)_{12}(SiO_2)_{12}] \cdot 30 H_2O$ $K_9Na_3[(AlO_2)_{12}(SiO_2)_{12}] \cdot 27 H_2O$ The zeolites indicated can also be lower in water content, or anhydrous. Further suitable zeolites are:

$Na_2O \cdot Al_2O_3 \cdot (2 \text{ to } 5) SiO_2 \cdot (3.5 \text{ to } 10) H_2O$ [zeolite P]

$Na_2O \cdot Al_2O_3 \cdot 2 SiO_2 \cdot (3.5-10)H_2O$ (zeolite MAP)

or the zeolites preparable by complete or partial replacement of the Na atoms by Li, K or H atoms, such as $(Li,Na,K,H)_{10}Al_{10}Si_{22}O_{64} \cdot 20 H_2O$.

$K_9Na_3[(AlO_2)_{12}(SiO_2)_{12}] \cdot 27 H_2O$ $K_4Al_4Si_4O_{16} \cdot 6H_2O$ [zeolite K-F]

$Na_8Al_8Si_{40}O_{96} \cdot 24H_2O$ [zeolite D], as described in Barrer et al., J. Chem. Soc. 1952, 1561–71, and in U.S. Pat. No. 2,950,952;

Also suitable are the following zeolites:

K offretite, as described in EP-A-400,961;

zeolite R, as described in GB 841,812;

zeolite LZ-217, as described in U.S. Pat. No. 4,503,023;

Ca-free zeolite LZ-218, as described in U.S. Pat. No. 4,333,859;

zeolite T, zeolite LZ-220, as described in U.S. Pat. No. 4,503,023;

$Na_3K_6Al_9Si_{27}O_{72} \cdot 21 H_2O$ [zeolite L];

zeolite LZ-211, as described in U.S. Pat. No. 4,503,023;

zeolite LZ-212, as described in U.S. Pat. No. 4,503,023;

zeolite O, zeolite LZ-217, as described in U.S. Pat. No. 4,503,023;

zeolite LZ-219, as described in U.S. Pat. No. 4,503,023;

zeolite Rho, zeolite LZ-214, as described in U.S. Pat. No. 4,503,023;

zeolite ZK-19, as described in Am. Mineral. 54 1607 (1969);

zeolite W (K-M), as described in Barrer et al., J. Chem. Soc. 1956, 2882, $Na_{30}Al_{30}Si_{66}O_{192} \cdot 98 H_2O$ [zeolite ZK-5, zeolite Q]

Particular preference is given to zeolite P grades of the above formula in which x is from 2 to 5 and y is from 3.5 to 10, and very particular preference is given to zeolite MAP of the standard formula in which x is 2 and y is from 3.5 to 10. In particular, the zeolite concerned is zeolite Na-P, i.e. M is Na. This zeolite generally occurs in the variants Na-P-1, Na-P-2 and Na-P-3, which differ in their cubic, tetragonal or orthorhombic structure (R. M. Barrer, B. M. Munday, J. Chem. Soc. A 1971, 2909–14). The literature reference just referred to also describes the preparation of zeolite P-1 and P-2. According to that reference, Zeolite P-3 is very rare and is therefore of virtually no practical interest. The structure of the zeolite P-1 corresponds to the gismondite structure known from the abovementioned Atlas of Zeolite Structures. In recent literature (EP-A-384 070) a distinction is made between cubic (zeolite B or $P_c$) and tetragonal (zeolite $P_1$) zeolites of the P type. Also mentioned therein are relatively new zeolites of the P type having Si:Al ratios below 1.07:1. These are zeolites having the designation MAP or MA-P, for "Maximum Aluminum P".

Depending on the preparation process, zeolite P may also include small fractions of other zeolites. Highly pure zeolite P has been described in WO 94/26662. Within the scope of the invention it is also possible to use those finely divided, water-insoluble sodium aluminosilicates which have been precipitated and crystallized in the presence of water-soluble organic or inorganic dispersants. These can be introduced into the reaction mixture in any desired manner, prior to or during the precipitation and crystallization.

Very particular preference is given to Na zeolite A and Na zeolite P.

The hydrotalcites and/or zeolites can be employed in amounts, for example, from 0.1 to 20, judiciously from 0.1 to 10 and, in particular, from 0.1 to 5 parts by weight per 100 parts by weight of halogen-containing polymer.

Further customary additives can also be added to the compositions of the invention, such as stabilizers, auxiliaries and processing aids, examples being alkali metal compounds and alkaline earth metal compounds, lubricants, plasticizers, pigments, fillers, phosphites, thiophosphites and thiophosphates, mercaptocarboxylic esters, epoxidized fatty acid esters, antioxidants, UV absorbers and light stabilizers, optical brighteners, impact modifiers and processing aids, gelling agents, antistats, biocides, metal passivators, flame retardants and blowing agents, antifog agents, compatibilizers and antiplateouts agents. (cf. "Handbook of PVC Formulating" by E. J. Wickson, John Wiley & Sons, New York 1993). Examples of such additives are as follows:

I. Fillers

Fillers (HANDBOOK OF PVC FORMULATING E. J. Wickson, John Wiley & Sons, Inc., 1993, pp. 393–449) and reinforcing agents (TASCHENBUCH der KUNSTSTOFFADDITIVE, R. Gächter & H. Mëller, Carl Hanser, 1990, pp. 549–615) are, for example, calcium carbonate, dolomite, wollastonite, magnesium oxide, magnesium hydroxide, silicates, china clay, talc, glass fibers, glass beads, wood flour, mica, metal oxides, or metal hydroxides, carbon black, graphite, rock flour, heavy spar, glass fibers, talc, kaolin and chalk. Chalk is preferred. The fillers can be employed in an amount of preferably at least 1 part, for example, from 5 to 200, judiciously from 10 to 150 and, in particular, from 15 to 100 parts by weight per 100 parts by weight of PVC.

II. Metal soaps

Metal soaps are primarily metal carboxylates of preferably relatively long-chain carboxylic acids. Familiar examples are stearates and laurates, and also oleates and salts of shorter-chain alkanecarboxylic acids. Alkylbenzoic acids are also said to be included under metal soaps. Metals which may be mentioned are Li, Na, K, Mg, Ca, Sr, Ba, Zn, Al, La, Ce and rare earth metals. Use is often made of what are known as synergistic mixtures, such as barium/zinc, magnesium/zinc, calcium/zinc or calcium/magnesium/zinc stabilizers. The metal soaps can be employed individually or in mixtures. A review of common metal soaps is given in Ullmann's Encyclopedia of Industrial Chemistry, 5$^{th}$ Ed., Vol. A16 (1985), p. 361 ff.). It is judicious to use organic metal soaps from the series of the aliphatic saturated $C_2$–$C_{22}$ carboxylates, the aliphatic unsaturated $C_3$–$C_{22}$ carboxylates, the aliphatic $C_2$–$C_{22}$ carboxylates substituted by at least one OH group, the cyclic and bicyclic carboxylates having 5–22 carbon atoms, the unsubstituted benzenecarboxylates substituted by at least one OH group and/or by $C_1$–$C_{16}$-alkyl, the unsubstituted naphthalenecarboxylates substituted by at least one OH group and/or by $C_1$–$C_{16}$-alkyl, the phenyl $C_1$–$C_{16}$-alkylcarboxylates, the naphthyl $C_1$–$C_{16}$-alkylcarboxylates or the unsubstituted or $C_1$–$C_{12}$-alkyl-substituted phenolates, tallates and resinates.

Named examples which may be mentioned are the zinc, calcium, magnesium or barium salts of monovalent carboxylic acids such as acetic, propionic, butyric, valeric, hexanoic, enanthoic, octanoic, neodecanoic, 2-ethylhexanoic, pelargonic, decanoic, undecanoic, dodecanoic, tridecanoic, myristic, palmitic, isostearic, stearic, 12-hydroxystearic, behenic, benzoic, p-tert-butylbenzoic, N,N-dimethylhydroxybenzoic, 3,5-di-tert-butyl-4-hydroxybenzoic, toluic, dimethylbenzoic, ethylbenzoic, n-propylbenzoic, salicylic, p-tert-octylsalicyclic and sorbic acid; calcium, magnesium and zinc salts of the monoesters of divalent carboxylic acids such as oxalic, malonic, succinic, glutaric, adipic, fumaric, pentane-1,5-dicarboxylic, hexane-1,6-dicarboxylic, heptane-1,7-dicarboxylic, octane-1,8-dicarboxylic, phthalic, isophthalic, terephthalic and hydroxyphthalic acid; and of the di- or triesters of tri- or tetravalent carboxylic acids such as hemimellitic, trimellitic, pyromellitic and citric acid.

Preference is given to calcium, magnesium and zinc carboxylates of carboxylic acids having 7 to 18 carbon atoms (metal soaps in the narrow sense), such as, for example, benzoates or alkanoates, preferably stearate, oleate, laurate, palmitate, behenate, hydroxystearates, dihydroxystearates or 2-ethylhexanoate. Particular preference is given to stearate, oleate and p-tert-butylbenzoate. Overbased carboxylates, such as overbased zinc octoate, are also preferred. Preference is likewise given to overbased calcium soaps.

If desired, it is also possible to employ a mixture of carboxylates of different structures.

Preference is given to compositions, as described, comprising an organozoic and/or organocalcium compound.

In addition to the compounds mentioned, organoaluminum compounds are also suitable, as are compounds analogous to those mentioned above, especially aluminum tristearate, aluminum distearate and aluminum monostearate, and also aluminum acetate and basic derivatives derived therefrom.

Further information on the aluminum compounds which can be used and are preferred is given in U.S. Pat. No. 4,060,512 and U.S. Pat. No. 3,243,394.

Also suitable in addition to the compounds already mentioned are organic rare earth compounds, especially compounds analogous to those mentioned above. The term rare earth compound means especially compounds of the elements cerium, praseodymium, neodymium, samarium, europium, gadolinium, terbium, dysprosium, holmium, erbium, thulium, ytterbium, lutetium, lanthanum and yttrium, mixtures—especially with cerium—being preferred. Further preferred rare earth compounds can be found in EP-A-0 108 023.

It is possible if desired to employ a mixture of zinc, alkali metal, alkaline earth metal, aluminum, cerium, lanthanum or lanthanoid compounds of different structure. It is also possible for organozinc, organoaluminum, organocerium, organo-alkali metal, organo-alkaline earth metal, organolanthanum or organolanthanoid compounds to be coated on an alumo salt compound; in this regard see also DE-A-4 031 818.

The metal soaps and/or mixtures thereof can be employed in an amount of, for example, from 0.001 to 10 parts by weight, judiciously from 0.01 to 8 parts and, with particular preference, from 0.05 to 5 parts by weight per 100 parts by weight of PVC. The same applies to the further metal stabilizers:

III. Further metal stabilizers

Here, mention may be made in particular of the organotin stabilizers. These can be the carboxylates, mercaptides and sulfides, in particular. Examples of suitable compounds are described in U.S. Pat. No. 4,743,640.

IV. Alkali metal and alkaline earth metal compounds

By these are meant principally the carboxylates of the above-described acids, but also corresponding oxides and/or hydroxides or carbonates. Also suitable are mixtures thereof with organic acids. Examples are LiOH, NaOH, KOH, CaO, Ca(OH)$_2$, MgO, Mg(OH)$_2$, Sr(OH)$_2$, Al(OH)$_3$, CaCO$_3$ (also basic carbonates, such as magnesia alba and hutite), and also Na and K salts of fatty acids. In the case of alkaline earth metal and Zn carboxylates it is also possible to employ their adducts with MO or M(OH)$_2$ (M=Ca, Mg, Sr or Zn), known as "overbased" compounds. In addition to the stabilizer combination of the invention it is preferred to employ alkali metal carboxylates, alkaline earth metal carboxylates and/or aluminum carboxylates.

V. Lubricants

Examples of lubricants are montan wax, fatty acid esters, PE waxes, amide waxes, chlorinated paraffins, glycerol esters or alkaline earth metal soaps. Lubricants which can be used are also described in "Kunststoffadditive", R. G ächter/H. Müller, Carl Hanser Verlag, 3rd Ed., 1989, pages 478–488. Mention may also be made of fatty ketones (as described in DE 4 204 887) and of silicone-based lubricants (as described in EP 0 225 261) or combinations thereof, as set out in EP 0 259 783. Calcium stearate is preferred. The lubricants can also be applied to an alumo salt compound; in this regard see also DE-A-4 031 818.

VI. Plasticizers

Examples of suitable organic plasticizers are those from the following groups:

A) Phthalates: examples of such plasticizers are dimethyl, diethyl, dibutyl, dihexyl, di-2-ethylhexyl, di-n-octyl, diisooctyl, diisononyl, diisodecyl, diisotridecyl, dicyclhexyl, dimethylcyclohexyl, dimethylglycol, dibutylglycol, benzyl butyl and diphenyl phthalates, and also mixtures of phthalates, such as $C_7$–$C_9$- and $C_9$–$C_{11}$-alkyl phthalates obtained from predominantly linear alcohols, $C_6$–$C_{10}$-n-alkyl phthalates and $C_8$–$C_{10}$-n-alkyl phthalates. Of these preference is given to dibutyl, dihexyl, di-2-ethylhexyl, di-n-octyl, diisooctyl, diisononyl, diisodecyl, diisotridecyl and benzyl butyl phthalate, and the stated mixtures of alkyl phthalates. Particular preference is given to di-2-ethylhexyl, diisononyl and diisodecyl phthalate, which are also known by the common abbreviations DOP (dioctyl phthalate, di-2-ethylhexyl phthalate), DINP (diisononyl phthalate) and DIDP (diisodecyl phthalate).

B) Esters of aliphatic dicarboxylic acids, especially esters of adipic, azelaic and sebacic acid: examples of such plasticizers are di-2-ethylhexyl adipate, diisooctyl adipate (mixture), diisononyl adipate (mixture), diisodecyl adipate (mixture), benzyl butyl adipate, benzyl octyl adipate, di-2-ethylhexyl azelate, di-2-ethylhexyl sebacate and diisodecyl sebacate (mixture). Di-2-ethylhexyl adipate and diisooctyl adipate are preferred.

C) Trimellitates, examples being tri-2-ethylhexyl trimellitate, triisodecyl trimellitate (mixture), triisotridecyl trimellitate, triisooctyl trimellitate (mixture) and also tri-$C_6$–$C_8$-alkyl, tri-$C_6$–$C_{10}$-alkyl, tri-$C_7$–$C_9$-alkyl- and tri-$C_9$–$C_{11}$-alkyl trimellitates. The latter trimellitates are formed by esterification of trimellitic acid with the corresponding alkanol mixtures. Preferred trimellitates are tri-2-ethylhexyl trimellitate and the abovementioned trimellitates from alkanol mixtures. Customary abbreviations are TOTM (trioctyl trimellitate, tri-2-ethylhexyl trimellitate), TIDTM (triisodecyl trimellitate) and TITDTM (triisotridecyl trimellitate).

D) Epoxy plasticizers: these are primarily epoxidized unsaturated fatty acids, such as epoxidized soybean oil.

E) Polymer plasticizers: a definition of these plasticizers and examples of them are given in "Kunststoffadditive", R. Gächter/H. Müller, Carl Hanser Verlag, 3rd ed., 1989, section 5.9.6, pages 412–415, and also in "PVC Technology", W. V. Titow, 4th ed., Elsevier Publ., 1984, pages 165–170. The most common starting materials for preparing the polyester plasticizers are dicarboxylic acids, such as adipic, phthalic, azelaic and sebacic acids; diols, such as 1,2-propanediol, 1,3-butanediol, 1,4-butanediol, 1,6-hexanediol, neopentyl glycol and diethylene glycol.

F) Phosphoric esters: a definition of these esters is given in the abovementioned "Taschenbuch der Kunststoffadditive" section 5.9.5, pp. 408–412. Examples of such phosphoric esters are tributyl phosphate, tri-2-ethylbutyl phosphate, tri-2-ethylhexyl phosphate, trichloroethyl phosphate, 2-ethylhexyl diphenyl phosphate, cresyl diphenyl phosphate; triphenyl phosphate, tricresyl phosphate and trixylenyl phosphate. Preference is given to tri-2-ethylhexyl phosphate and to ®Reofos 50 and 95 (Ciba Spezialitätenchemie).

G) Chlorinated hydrocarbons (paraffins)

H) Hydrocarbons

I) Monoesters, e.g., butyl oleate, phenoxyethyl oleate, tetrahydrofurfuryl oleate and alkylsulfonic esters.

J) Glycol esters, e.g., diglycol benzoates.

Definitions and examples of plasticizers of groups G) to J) are given in the following handbooks:

"Kunststoffadditive", R. Gächter/H. Müller, Carl Hanser Verlag, 3rd ed., 1989, section 5.9.14.2, pp. 422–425, (group G), and section 5.9.14.1, p. 422, (group H).

"PVC Technology", W. V. Titow, 4th ed., Elsevier Publishers, 1984, section 6.10.2, pages 171–173, (group G), section 6.10.5 page 174, (group H), section 6.10.3, page 173, (group I) and section 6.10.4, pages 173–174 (group J). It is also possible to use mixtures of different plasticizers. The plasticizers can be employed in an amount of, for example, from 5 to 20 parts by weight, judiciously from 10 to 20 parts by weight, per 100 parts by weight of PVC. Rigid or semirigid PVC contains preferably up to 10%, with particular preference up to 5%, or no plasticizer.

VII. Pigments

Suitable substrates are known to the person skilled in the art. Examples of inorganic pigments are $TiO_2$, zirconium oxide-based pigments, $BaSO_4$, zinc oxide (zinc white) and lithopones (zinc sulfide/barium sulfate), carbon black, carbon black/titanium dioxide mixtures, iron oxide pigments, $Sb_2O_3$, $(Ti,Ba, Sb)O_2$, $Cr_2O_3$, spinels, such as cobalt blue and cobalt green, $Cd(S,Se)$, ultramarine blue. Organic pigments are, for example, azo pigments, phthalocyanine pigments, quinacridone pigments, perylene pigments, diketopyrrolopyrrole pigments and anthraquinone pigments. Preference is also given to $TiO_2$ in micronized form. A definition and further descriptions are given in "Handbook of PVC Formulating", E. J. Wickson, John Wiley & Sons, New York, 1993.

VIII. Phosphites (phosphorous triesters

Examples are triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy-pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, bis (2,4-di-tert-butyl-6-methylphenyhl) methyphenyl) methyl phosphite, bis(2,4-di-tert-butyl-6-methylphenyl) ethyl phosphite. Particularly suitable are trioctyl, tridecyl, tridodecyl, tritetradecyl, tristearyl, trioleyl, triphenyl, tricresyl, tris-p-nonylphenyl or tricylcohexyl phosphite and, with particular preference, the aryl dialkyl and alkyl diaryl phosphites, examples being phenyl didecyl, 2,4-di-tert-butylphenyl didodecyl phosphite, 2,6-di-tert-butylphenyl didodecyl phosphite and the dialkyl and diaryl pentaerythritol diphosphites, such as distearyl pentaerythritol diphosphite, and also nonstoichiometric triaryl phosphites whose composition is, for example, $(H_{19}C_9-C_6H_4)O_{1.5}P(OC_{12,13}H_{25,27})_{1.5}$ or $(H_8C_{17-C_6}H_4)O_2P(i-C_8H_{17}O)$ or $(H_{19}C_{9-C_6}H_4)O_{1.5}P(OC_{9,11}H_{19,23})_{1.5}$ or

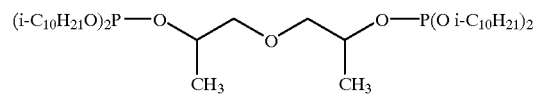

Preferred organic phosphites are distearyl pentaerythritol diphosphite, trisnonylphenyl phosphite and phenyl didecyl phosphite. Other suitable phosphites are phosphorous diesters (with abovementioned radicals) and phosphorous monoesters (with abovementioned radicals), possibly in the form of their alkali metal, alkaline earth metal, zinc or aluminum salts. It is also possible for these phosphorous esters to have been applied to an alumo salt compound; in this regard see also DE-A-4 031 818.

The organic phosphites can be employed in an amount of, for example, from 0.01 to 10, judiciously from 0.05 to 5 and, in particular, from 0.1 to 3 parts by weight per 100 parts by weight of PVC.

IX. Thiophosphites and thiophosphates

By thiophosphites and thiophosphates are meant compounds of the general type $(RS_3P$, $(RS_3P=O$ and $(RS)_3P=S$, respectively, as are described, for instance, in the patents DE 2 809 492, EP 0 090 770 and EP 0 573 394. Examples of these compounds are trithiohexyl phosphite, trithiooctyl phosphite, trithiolauryl phosphite, trithiobenzyl phosphite, trithiophosphorous acid tris(carbo-i-octyloxy) methyl ester, trithiophosphorous acid tris (carbotrimethylcyclohexyloxy)methyl ester, trithiophosphoric acid S,S,S-tris(carbo-i-octyloxy)methyl ester, trithiophosphoric acid S,S,S-tris(carbo-2-ethylhexyloxy)

methyl ester, trithiophosphoric acid S,S,S-tris-1-(carbohexyloxy)ethyl ester, trithiophosphoric acid S,S,S-tris-1-(carbo-2-ethylhexyloxy)ethyl ester and trithiophosphoric acid S,S,S-tris-2-(carbo-2-ethylhexyloxy)ethyl ester.

X. Mercaptocarboxylic esters

Examples of these compounds are esters of thioglycolic acid, thiomalic acid, mercaptopropionic acid, the mercaptobenzoic acids and thiolactic acid, mercaptoethyl stearate and mercaptoethyl oleate, as are described in patents FR 2459 816, EP 0 090 748, FR 2 552 440 and EP 0 365 483. The generic mercaptocarboxylic esters also embrace polyol esters and partial esters thereof, and also thioethers derived from them.

XI. Epoxidized fatty acid esters and other epoxy compounds

The stabilizer combination of the invention may additionally comprise preferably at least one epoxidized fatty acid ester. Particularly suitable such esters are those of fatty acids from natural sources (fatty acid glycerides), such as soybean oil or rapeseed oil. It is, however, also possible to employ synthetic products such as epoxidized butyl oleate. Epoxidized polybutadiene and polyisoprene can also be used, as they are or in partially hydroxylated form, or else homo- or copolymeric glycidyl acrylate and glycidyl methacrylate can be used. These epoxy compounds can also have been applied to an alumo salt compound; in this regard see also DE-A-4 031 818.

XII. Antioxidants

Examples of suitable such compounds are:

Alkylated monophenols, for example, 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-di-cyclopentyl-4-methylphenol, 2-(alpha-methylcyclohexyl)-4,6-dimethylphenol, 2,6-di-octadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)phenol, 2,4-dimethyl-6-(1'-methylheptadex-1'-yl) phenol, 2,4-dimethyl-6-(1'-methyltridec-1'-yl)phenol, octylphenol, nonylphenol, dodecylphenol and mixtures thereof.

Alkylthiomethylphenols, for example, 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

Alkylated hydroquinones, for example, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

Hydroxylated thiodiphenyl ethers, for example, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol)-4, 4'-bis(2,6-dimethyl-4-hydroxyphenyl) disulfide.

Alkylidenebisphenols, for example, 2,2'-methylenebis(6-tert-butyl-4-methylphenol), 2,2'-methylenebis(6-tert-butyl-4-ethylphenol), 2,2'-methylenebis[4-methyl-6-(alpha-methylcyclohexyl)phenol], 2,2'-methylenebis (4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(alpha-methylbenzyl)-4-nonylphenol], 2,2'-methylenebis[6-(alpha,alpha-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol 1,1,3-tris(5-tert-butyl-4-hydroxy-2-methyl-phenyl)butane, 1,1-bis-(5-tert-butyl-4-hydroxy-2-methylphenyl)-3-n-dodecylmercaptobutane, ethylene glycol bis[3,3-bis-(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl)butane, 2,2-bis(3,5-di-tert-butyl-4-hydroxyphenyl)propane, 2,2-bis(4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

Benzyl compounds, for example, 3,5,3',5'-tetra-tert-butyl-4,4'-dihydroxy-dibenzyl ether, octadecyl, 4-hydroxy-3,5-dimethylbenzyl-mercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl) sulfide, isooctyl, 3,5-di-tert-butyl-4-hydroxybenzyl-mercaptoacetate.

Hydroxybenzylated malonates, for example, dioctadecyl 2,2-bis(3,5-di-tert-butyl-2-hydroxybenzyl)malonate, dioactadecyl 2-(3-tert-butyl-4-hydroxy-5-methylbenzyl)malonate, didodecyl mercaptoethyl-2,2-bis(3,5-di-tert-butyl-4-hydroxybenzyl)malonate, di[4-(1,1,3,3-tetramethylbutyl)-phenyl] 2,2-bis(3,5-di-tert-butyl-4-hydroxybenzyl)malonate.

Aromatic hydroxybenzyl compounds, for example, 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

Triazine compounds, for example, 2,4-bisoctylmercapto-6-(3,5-di-tert-butyl-4-hydroxyanilino)-1,3,5-triazine, 2-octylmercapto-4,6-bis-(3,5-di-tert-butyl-4-hydroxyanilino)-1,3,5-triazine, 2-octylmercapto-4,6-bis-(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris-(3,5-dicyclohexyl-4-hydroxybenzyl) isocyanurate.

Phosphates and phosphonites, for example, dimethyl 2,5-di-tert-butyl-4-hydroxybenzylphosphonate, diethyl 3,5-di-tert-butyl-4-hydroxy-benzylphosphonate, dioctadecyl 3,5-di-tert-butyl-4-hydroxybenzylphosphonate, dioctadecyl 5-tert-butyl-4-hydroxy-3-methylbenzylphosphonate, Ca salt of monoethyl 3,5-di-tert-butyl-4-hydroxybenzylphosphonate, tetrakis(2,4-di-tertbutylphenyl)-4,4'-biphenylenediphosphonite, 6-isooctyloxy-2,4,8,10-tetra-tert-butyl-12H-dibenz[d,g]-1,3,2-dioxaphosphocine, 6-fluoro-2,4,8,10-tetra-tert-butyl-12-methyl-dibenz[d,g]-1,3,2-dioxaphosphocine.

Acylaminophenols, for example, 4-hydroxylauranilide, 4-hydroxystearanilide, octyl N-(3,5-di-tert-butyl-4-hydroxyphenyl)carbamate.

Esters of beta-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propane diol, neopentyl glycol, thiodiethylene glycol, diethylene glycol, triethylene glycol, pentaerythritol, dipentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, ditrimethylolpropane, 4-hydroxymethyl-1-phospha-2,6,7-trioxabicyclo[2.2.2]octane.

Esters of beta-(5-tert-butyl-4-hydroxy-3-methylphenyl) propionic acid with mono- or polyhydric alcohols, for example, with methanol, ethanol, octanol, octadecanol, 1,6-hexanediol, 1,9-nonanediol, ethylene glycol, 1,2-propanediol neopentyl glycol, thiodiethylene glycol, diethylene glycol, triethylene glycol, pentaerythritol, tris(hydroxy)ethyl isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

Esters of beta-(3,5-dicyclohexyl-4-hydroxyphenyl) propionic acid with mono- or polyhydric alcohols, for example, with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pantaerythritol, tris(hydroxy)ethyl isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

Esters of 3,5-di-tert-butyl-4-hydroxyphenylacetic acid with mono- or polyhydric alcohols, for example, with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxy)ethyl isocyanurate, N,N'-bis(hydroxyethyl)oxalamide, 3-thiaundecanol, 3-thiapentadecanol, trimethylhexanediol, trimethylpropane, 4-hydroxymethyl-1-phospha-2,6,7-trioxabicyclo[2.2.2]octane.

Amides of beta-(3,5-di-tert-butyl-4-hydroxyphenyl) propionic acid, such as, for example, N,N'-bis(3,5-di-tert-butyl-4-hydroxyphenylpropionyl) hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl) hydrazine.

Vitamin E (tocopherol) and derivatives.

Preference is given to antioxidants of groups 1–5, 10 and 12, especially 2,2-bis(4-hydroxyphenyl)propane, esters of 3,5-di-tert-butyl-4-hydroxyphenylpropionic acid with octanol, octadecanol or pentaerythritol or tris(2,4-di-tert-butylphenyl) phosphite. It is also possible, if desired, to employ a mixture of antioxidants of different structures.

The antioxidants can be employed in an amount of, for example, from 0.01 to 10 parts by weight judiciously from 0.1 to 10 parts by weight and in particular, from 0.1 to 5 parts by weight per 100 parts by weight of PVC.

XIII. UV absorbers and light stabilizers

Examples of these are:

2-(2'-Hydroxyphenyl)benzotriazoles, such as, for example 2-(2'-hydroxy-5'-methylphenyl)benzotriazole, 2-(3',5'-di-tert-butyl-2'-hydroxyphenyl)benzo-triazole, 2-(5'-tert-butyl-2-2'-hydroxyphenyl)benzotriazole, 2-(2'-hydroxy-5'-(1,1,3,3-tetramethylbutyl)phenyl) benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(alpha,alpha-dimethylbenzyl)-2'-hydroxyphenyl) benzotriazole, mixtures of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotri-azole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl] benzotriazole with polyethylene glycol 300; where R=3'-tert-butyl-4'-hydroxy-5'-2H-benzotriazol-2-yl-phenyl.

2-Hydroxybenzophenones, for example the 4-hydroxy, 4-methoxy, 4-octoxy, 4-decyloxy, 4-dodecyloxy, 4-benzyloxy, 4,2',4'-trihydroxy, 2'-4,4'-dimethoxy derivative.

Esters of substituted or unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxy-benzoate.

Acrylates, for example ethyl alpha-cyano-beta,beta-diphenylacrylate or isooctyl-ethyl alpha-cyano-beta, beta-diphenylacrylate, methyl alpha-carbomethoxycinnamate, methyl alpha-cyano-beta-methyl-p-methoxycinnamate or butyl alpha-cyano-beta-methyl-p-methoxycinnamate, methyl alpha-carbomethoxy-p-methoxycinnamate, N-(beta-carbomethoxy-b-cyanovinyl)-2-methyl-indoline.

Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters such as the methyl or ethyl ester, of 4-hydroxy-3,5-di-tert-butylbenzylphosphonic acid, nickel complexes of ketoximes, such as of 2-hydroxy-4-methylphenyl undecyl ketoxime, nickel complexes of 1-phenyl-4-lauroyl-5-hydroxypyrazole, with or without additional ligands.

Oxalamides, for example 4,4'-dioctyloxyoxanilide, 2,2'-dioctyloxy-5,5'-di-tert-butyl-oxanilide, 2,2'-didodecyloxy-5,5'-di-tert-butyloxanilide, 2-ethoxy-2'-ethyl-oxanilide, N,N'-bis(3-dimethylaminopropyl) oxalamide, 2-ethoxy-5-tert-butyl-2'-ethyloxanilide and its mixture with 2-ethoxy-2'-ethyl-5,4'-di-tert-butyl-oxanilide, mixtures of o- and p-methoxy and of o- and p-ethoxy-di-substituted oxanilides.

2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxyprop-yloxy)phenyl]-4,6-bis(2,4-dimethylphenyl)-1,3,5-triazine.

Sterically hindered amines, for example bis(2,2,6,6-tetramethyl-piperidin-4-yl) sebacate, bis(2,2,6,6-tetramethylpiperidin-4-yl) succinate, bis(1,2,2,6,6-pentamethylpiperidin-4-yl) sebacate, bis(1-octyloxy-2,2,6,6-tetramethylpiperidin-4-yl) sebacate, bis(1,2,2,6,6-pentamethylpiperidyl) n-butyl-3,5-di-tert-butyl-4-hydroxybenzylmalonate, the condensate of 1-hydroxyethyl-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-di-(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidone-2,5-dione, 3-dodecyl-1-(1,2,2,6,6-pentamethyl-4-piperidyl)pyrrolidine-2,5-dione, mixtures of 4-hexadecyloxy- and 4-stearyloxy-2,2,6,6-tetramethylpiperidine, the condensate of N,N'-bis(2,2,6,6-tetramethyl-4-piperidyl)hexamethylendiamine and 4-cyclohexylamino-2,6-dichloro-1,3,5-triazine, the condensate of 1,2-bis(3-aminopropylamino)ethane and 2,4,6-trichloro-1,3,5-triazine, and also 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4.5]decane, the reaction product of 7,7,9,9-tetramethyl-2-cycloundecyl-1-oxa-3,8-diaza-4-oxospiro[4.5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, the diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]-siloxane, the reaction product of maleic anhydride-α-olefin copolymer and 2,2,6,6-tetramethyl-4-aminopiperidine or 1,2,2,6,6-pentamethyl-4-aminopiperidine.

XIV. Blowing agents

Examples of blowing agents are organic azo and hydrazo compounds, tetrazoles, oxazines, isatoic anhydride, and also sodium carbonate and sodium bicarbonate. Preference is given to azodicarboxamide and sodium bicarbonate and mixtures thereof.

Definitions and examples of impact modifiers and processing aids, gelling agents, antistats, biocides, metal passivators, optical brighteners, flame retardants, antifogging agents and compatibilizers are described in "Kunststoffadditive", R. Gächter/H. Müller, Carl Hanser Verlag, 3rd ed., 1989, and in the "Handbook of Polyvinyl Chloride Formulating" E. J. Wickson, J. Wiley & Sons, 1993, and in "Plastics Additives" G. Pritchard, Chapman & Hall, London, 1st ed., 1998. Impact modifiers are also described in detail in "Impact Modifiers for PVC", J. T. Lutz/D. L. Dunkelberger, John Wiley & Sons, 1992.

XV. beta-Diketones, beta-keto esters 1,3-dicarbonyl compounds which can be used may be linear or cyclic dicarbonyl compounds. Preference is given to the use of dicarbonyl compounds of the following formulae: $R'_1CO\ CHR'_2—COR'_3$ in which $R'_1$ is $C_1–C_{22}$-alkyl, $C_5–C_{10}$-hydroxyalkyl, $C_2–C_{18}$-alkenyl, phenyl, OH—, $C_1–C_4$-alkyl-, $C_1–C_4$-alkoxy- or halogen-substituted phenyl, $C_7–C_{10}$-phenylalkyl, $C_5–C_{12}$-cycloalkyl, $C_1–C_4$-alkyl-substituted $C_5–C_{12}$-cycloalkyl or a group —$R'_5$—S—$R'_6$ or —$R'_5$—O—$R'_6$, $R'_2$ is hydrogen, $C_1–C_8$-alkyl, $C_2–C_{12}$-alkenyl, phenyl, $C_7–C_{12}$-alkylphenyl, $C_7–C_{10}$-phenylalkyl or a group —CO—$R'_4$, $R'_3$ is as defined for $R'_1$ or is $C_1–C_{18}$-alkoxy, $R'_4$ is $C_1–C_4$-alkyl or phenyl, $R_5$ is $C_1–C_{10}$-alkylene and $R'_6$ is $C_1–C_{12}$-alkyl, phenyl, $C_7–C_{18}$-alkylphenyl or $C_7–C_{10}$-phenylalkyl.

These include the hydroxyl-containing diketones of EP 0 346 279 and the oxa and thia diketones of EP 0 307 358, as well as the keto esters based on isocyanic acid, of U.S. Pat. No. 4,339,383.

$R'_1$ and $R'_3$ as alkyl can in particular be $C_1–C_{18}$-alkyl, such as, for example methyl, ethyl, n-propyl, isopropyl, n-butyl, tert-butyl, pentyl, hexyl, heptyl, octyl, decyl, dodecyl or octadecyl.

$R'_1$ and $R'_3$ as hydroxyalkyl are in particular a group —$(CH_2)_n$—OH in which n is 5, 6 or 7.

$R'_1$ and $R'_3$ as alkenyl can for example be vinyl, allyl, methallyl, 1-butenyl, 1-hexenyl or oleyl, preferably allyl.

$R'_1$ and $R'_3$ as OH-, alkyl-, alkoxy- or halogen-substituted phenyl can for example be tolyl, xylyl, tert-butylphenyl, methoxyphenyl, ethoxyphenyl, hydroxyphenyl, chlorophenyl or dichlorophenyl.

$R'_1$ and $R'_3$ as phenylalkyl are in particular benzyl. $R'_2$ and $R'_3$ as cycloalkyl or alkylcycloalkyl are, in particular, cyclohexyl or methylcyclohexyl. $R'_2$ as alkyl can in particular be $C_1$–$C_4$-alkyl. $R'_2$ as $C_2$–$C_{12}$-alkenyl can in particular be allyl. $R'_2$ as alkylphenyl can in particular be tolyl. $R'_2$ as phenylalkyl can in particular be benzyl. Preferably, $R'_2$ is hydrogen. $R'_3$ as alkoxy can for example be methoxy, ethoxy, butoxy, hexyloxy, octyloxy, dodecyloxy, tridecyloxy, tetradecyloxy or octadecyloxy. $R'_5$ as $C_1$–$C_{10}$-alkylene is, in particular, $C_2$–$C_4$-alkylene. $R'_6$ as alkyl is, in particular, $C_4$–$C_{12}$-alkyl, such as, for example butyl, hexyl, octyl, decyl or dodecyl. $R'_6$ as alkylphenyl is in particular tolyl. $R'_6$ as phenylalkyl is in particular benzyl. Examples of 1,3-dicarbonyl compounds of the above formula and their alkali metal, alkaline earth metal and zinc chelates are acetylacetone, butanoylacetone, heptanoylacetone, sterolyacetone, palmitoylacetone, lauroylacetone, 7-tert-nonylthio-2,4-heptanedione, benzoylacetone, dibenzoylmethane, lauroylbenzoylmethane, palmitoylbenzoylmethane, stearoylbenzoylmethane, isooctylbenzoylmethane, 5-hydroxycapronyl-benzoylmethane, tribenzoylmethane, bis(4-methylbenzoyl)methane, benzoyl-p-chlorobenzoylmethane, bis(2-hydroxybenzoyl)methane, 4-methoxybenzoyl-benzoylmethane, bis(4-methoxybenzoyl)methane, 1-benzoyl-1-acetylnonane, benzoylacetylphenylmethane, stearoyl-4-methoxybenzoylmethane, bis(4-tert-butylbenzoyl)methane, benzoylformylmethane, benzoylphenylacetylmethane, biscyclohexanoylmethane, di-pivaloylmethane, 2-acetylcyclopentanone, 2-benzoylcyclopentanone, methyl, ethyl and allyl diacetoacetate, methyl and ethyl benzoyl-, propionyl- and butyrylacetoacetate, triacetylmethane, methyl, ethyl, hexyl, octyl, dodecyl or octadecyl acetoacetate, methyl, ethyl, butyl, 2-ethylhexyl, dodecyl or octadecyl benzoylacetate, and also $C_1$–$C_{18}$-alkyl propionylacetates and butyrylacetates; ethyl, propyl, butyl, hexyl or octyl stearoylacetate, and also polycyclic β-keto esters, as described in EP 0 433 230, and dehydraacetic acid, and the zinc, magnesium or alkali metal salts thereof.

Preference is given to 1,3-diketo compounds of the above formula in which $R'_1$ is $C_1$–$C_{18}$-alkyl, phenyl, OH-, methyl- or methoxy-substituted phenyl, $C_7$–$C_{10}$-phenylalkyl or cyclohexyl, $R'_2$ is hydrogen and $R'_3$ is as defined for $R'_1$. The 1,3-diketo compounds can be employed in amount of, for example, from 0.01 to 10, judiciously from 0.01 to 3 and, in particular, from 0.01 to 2 parts by weight per 100 parts by weight of PVC.

Examples of the chlorine-containing polymers to be stabilized are: polymers of vinyl chloride and of vinylidene chloride, vinyl resins comprising vinyl chloride units in their structure, such as copolymers of vinyl chloride, and vinyl esters of aliphatic acids, especially vinyl acetate, copolymers of vinyl chloride with esters of acrylic and methacrylic acid and with acrylonitrile, copolymers of vinyl chloride with diene compounds and unsaturated dicarboxylic acids or their anhydrides, such as copolymers of vinyl chloride with diethyl maleate, diethyl fumarate or maleic anhydride, post-chlorinated polymers and copolymers of vinyl chloride, copolymers of vinyl chloride and vinylidene chloride with unsaturated aldehydes, ketones and others, such as acrolein, crotonaldehyde, vinyl methyl ketone, vinyl methyl ether, vinyl isobutyl ether and the like; polymers of vinylidene chloride and its copolymers with vinyl chloride and other polymerizable compounds; polymers of vinyl chloroacetate and dichlorodivinyl ether; chlorinated polymers of vinyl acetate, chlorinated polymeric esters of acrylic acid and of alpha-substituted acrylic acid; polymers of chlorinated styrenes, for example dichlorostyrene; chlorinated rubbers; chlorinated polymers of ethylene; polymers and post-chlorinated polymers of chlorobutadiene and copolymers thereof with vinyl chloride, chlorinated natural and synthetic rubbers, and also mixtures of these polymers with one another or with other polymerizable compounds. In the context of this invention, PVC also embraces copolymers with polymerizable compounds such as acrylonitrile, vinyl acetate or ABS, which can be suspension, bulk or emulsion polymers. Preference is given to a PVC homopolymer, alone or in combination with polyacrylates. Also included are graft polymers of PVC with EVA, ABS and MBS. Preferred substrates are also mixtures of the abovementioned homo- and copolymers, especially vinyl chloride homopolymers, with other thermoplastic and/or elastomeric polymers, especially blends with ABS, MBS, NBR, SAN, EVA, CPE, MBAS, PMA, PMMA, EPDM and polyactones.

Examples of such components are compositions of (i) 20–80 parts by weight of a vinyl chloride homopolymer (PVC) and (ii) 80–20 parts by weight of at least one thermoplastic copolymer based on styrene and acrylonitrile, in particular from the group ABS, NBR, NAR, SAN and EVA. The abbreviations used for the copolymers are familiar to the person skilled in the art and have the following meanings: ABS: acrylonitrile-butadiene-styrene; SAN: styrene-acrylonitrile; NBR: acrylonitrile-butadiene; NAR: acrylonitrile-acrylate; EVA: ethylene-vinyl acetate. Also suitable in particular are acrylate-based styrene-acrylonitrile copolymers (ASA). Preferred components in this context are polymer compositions comprising as components (i) and (ii) a mixture of 25–75% by weight PVC and 75–25% by weight of the abovementioned copolymers. Examples of such compositions are: 24–50% by weight PVC and 75–50% by weight copolymers of 40–75% by weight PVC and 60–25% by weight copolymers. Preferred copolymers are ABS, SAN and modified EVA, especially ABS, NBR, NAR and EVA are also particularly suitable. In the composition of the invention it is possible for one or more of the abovementioned copolymers to be present. Particularly important components are compositions comprising (i) 100 parts by weight of PVC and (ii) 0–300 parts by weight of ABS and/or SAN-modified ABS and 0–80 parts by weight of the copolymers NBR, NAR and/or EVA, but especially EVA.

For stabilization in the context of this invention, further suitable polymers are, in particular, recyclates of chlorine-containing polymers, these polymers being the polymers described in more detail above that have also undergone damage through processing, use or storage. PVC recyclate is particularly preferred. The recyclates may also include small amounts of extraneous substances, such as, for example, paper, pigments, adhesives, which are often difficult to remove. These extraneous substances may also arise from contact with various materials in the course of use or reprocessing, examples being residues of fuel, fractions of coating material, traces of metal and residues of initiator.

Stabilization in accordance with the invention is of particular advantage in the context of PVC formulations as are customary for pipes and profiles. Stabilization can be effected without heavy metal compounds (Sn, Pb, Cd, Zn stabilizers). This characteristic offers advantages in certain fields, since heavy metals—with the exception of zinc at best—are often unwanted both during the production and during the use of certain PVC articles, on ecological grounds. The production of heavy metal stabilizers also often causes problems from an industrial hygiene standpoint. Similarly, the processing of ores containing heavy metals is frequently associated with serious effects on the environment, the environment here including the biosystem of humankind, animals (fish), plants, the air and soil. For these reasons, the incineration and landfilling of plastics containing heavy metals is also disputed.

The invention also relates to a method of stabilizing PVC, which comprises adding thereto at least one of the abovementioned stabilizer combinations.

The stabilizers can judiciously be incorporated by the following methods: as an emulsion or dispersion (one possibility, for example, is the form of a pastelike mixture. An advantage of the combination of the invention in the case of this form is the stability of the paste); as a dry mix in the course of the mixing of additional components or polymer mixtures; by direct addition to the processing apparatus (e.g. calenders, mixers, compounders, extruders and the like), or as a solution or melt or as flakes or pellets in dust-free form as a one-pack product.

The PVC stabilizer in accordance with the invention, to which the invention likewise relates, can be prepared in a manner known per se using devices known per se such as the abovementioned processing apparatus to mix the stabilizer combination of the invention and any further additives with the PVC. In this case, the stabilizers can be added individually or as a mixture or else in the form of so-called masterbatches.

The PVC stabilized in accordance with the present invention can be brought into the desired form by known methods. Examples of such methods are milling, calendering, extruding, injection molding or spinning, and also extrusion blow molding. The stabilized PVC can also be processed to foam materials.

A PVC stabilized in accordance with the invention is suitable, for example, for hollow articles (bottles), packaging films (thermoform sheets), blown films, pipes, foam materials, heavy profiles (window frames), transparent-wall profiles, construction profiles, sidings, fittings, office films and apparatus enclosures (computers, domestic appliances).

Preference is given to PVC rigid foam articles and PVC pipes for drinking water or wastewater, pressure pipes, gas pipes, cable-duct and cable protection pipes, pipes for industrial pipelines, seepage pipes, flowoff pipes, guttering pipes and drainage pipes. For further details on this subject see "Kunststoffhandbuch PVC", Vol. 2/2, W. Becker/H. Braun, 2nd ed., 1985, Carl Hanser Verlag, Pages 1236–1277.

6-Aminouracils are prepared by known methods [e.g., U.S. Pat. No. 2,598,936, WO 96/04280, J. Org. Chem. 16, 1879–1890 (1951), J. Org. Chem. 30, 656 (1965), JACS 82, 3973 (1960) and Synthesis 1996, page 459 ff.].

Compounds 1 to 25 prepared are summarized in Table 1.

As in the remainder of the text, parts and percentages are by weight unless stated otherwise.

TABLE 1

| Example | Y | $R_1$ | $R_2$ | $R_3$ | Yield | Melting point ° C. | Appearance |
|---|---|---|---|---|---|---|---|
| 1 | O | methyl | methyl | 2-methylphenyl | 61% | 158–159 (ethyl acetate) | pale gray crystals |
| 2 | O | methyl | methyl | 2,4-dimethylphenyl | 64% | 187–188 (ethyl acetate/n-PrOH) | beige crystals |
| 3 | O | methyl | methyl | 2,5-dimethylphenyl | 43% | 194–196 (crude product) | white crystals |
| 4 | O | methyl | methyl | 2-hydroxyphenyl | 77% | 228–231 (crude product) | white crystals |
| 5 | O | n-propyl | n-propyl | 2-hydroxyphenyl | 36% | 166–168 (i-PrOH/H$_2$O) | white crystals |
| 6 | O | n-butyl | n-butyl | 2-hydroxyphenyl | 35% | 142–144 (toluene) | white crystals |
| 7 | O | methyl | methyl | 3-hydroxyphenyl | 56% | 249–251 (toluene) | white crystals |
| 8 | O | methyl | methyl | 4-hydroxyphenyl | 65% | 265–270 (n-PrOH/H$_2$O) | light green crystals |
| 9 | O | methyl | methyl | 2-hydroxy-4-methylphenyl | 82% | 228–230 (i-PrOH/H$_2$O) | white crystals |
| 10 | O | methyl | methyl | 2-hydroxy-5-methylphenyl | 92% | 234–235 (n-PrOH/H$_2$O) | pale blue crystals |
| 11 | O | methyl | methyl | 2-hydroxy-5-t-butylphenyl | 80% | 227–230 crude product | white crystals |
| 12 | O | methyl | methyl | 2-methoxyphenyl | 78% | 227–229 (n-PrOH/H$_2$O) | white crystals |
| 13 | O | methyl | methyl | 4-methoxyphenyl | 40% | 167–168 (n-PrOH/H$_2$O) | white crystals |
| 14 | O | methyl | methyl | 3-ethoxycarbonyl-phenyl | 65% | 165–167 (n-PrOH) | white crystals |
| 15 | O | methyl | methyl | 4-ethoxycarbonyl-phenyl | 70% | 205–207 (n-PrOH) | white crystals |
| 16 | O | methyl | methyl | 1-naphthyl | 73% | 185–205 (n-PrOH) | beige crystals |
| 17 | O | methyl | methyl | benzyl | 79% | 145–146 (n-PrOH) | white crystals |
| 18 | O | methyl | methyl | 2-hydroxyethyl | 75% | 179–181 (MeOH/n-PrOH) | white crystals |
| 19 | O | methyl | methyl | 2-hydroxypropyl | 60% | 131–133 (ethyl acetate/MeOH) | white crystals |
| 20 | O | methyl | methyl | 2-hydroxyoctyl | 11% | 134–135 (ethyl acetate/petroleum ether) | yellow crystals |

TABLE 1-continued

| Example | Y | R₁ | R₂ | R₃ | Yield | Melting point ° C. | Appearance |
|---|---|---|---|---|---|---|---|
| 21 | O | methyl | methyl | 2-ethylhexyl | 51% | 61–63 crude product | light brown crystals |
| 22 | O | methyl | methyl | n-dodecyl | 41% | 92–94 (n-PrOH/H₂O) | white crystals |
| 23 | O | methyl | methyl | cyclohexyl | 68% | 160–162 (n-PrOH) | white crystals |
| 24 | O | methyl | methyl | 3-methoxyphenyl | 69% | 237–238 (n-PrOH/H₂O) | white crystals |
| 25 | O | methyl | methyl | 3-Hydroxypropyl | 63% | 143–144 crude product | white crystals |

Preparation Examples

Example 4

A 1 l 4-neck flask with KPG stirrer, air condenser, thermometer and bubble counter is charged under nitrogen with 155.2 g (1.0 mol) of 6-amino-1,3-dimethyluracil, 160 g (1.1 mol) of 2-aminophenol hydrochloride and 300 g of diethylene glycol dimethyl ether and this initial charge is stirred at 145–155° C. for 75 minutes. Subsequently, the reaction mixture is cooled to 10° C., the precipitated crystals are filtered off on a suction filter, and the filter product is washed twice with 100 ml of i-propanol each time. The crystals are dried in a vacuum drying cabinet at 80° C. This dried residue of 244.1 g is then stirred with 300 g of water for 30 minutes and the reaction product is filtered off with suction, washed with 100 g of water and dried.

Yield: 188.6 g (≈76.3% of theory) of white, crystalline powder (m.p. 228–230° C.)

Example 13

A mixture of 43.5 g (0.357 mol) of p-anisidine, 27.3 g (0.176 mol) of 6-amino-1,3-dimethyluracil and 20 g of 32% strength hydrochloric acid is heated to 150° C. with stirring over the course of 1.5 hours. During the heating phase, the water is distilled off. The reaction mixture is stirred at 150° C. for a further 1.5 hours, and then cooled to 90° C., 100 ml of methanol are added, and the mixture is heated at reflux for 30 minutes and then cooled to 5° C. The crystalline precipitate is filtered off with suction and subsequently recrystallized from a mixture of 200 ml of n-propanol/60 ml of water.

Yield: 18.3 g (≈40% of theory) of white crystals (m.p. 167–168° C.)

Example 18

26.2 g (0.15 mol) of 6-chloro-1,3-dimethyluracil, 20 g of ethanolamine and 50 ml of water are heated at 20° C. with stirring for 3 hours. After cooling to room temperature, the precipitated crystals are filtered off with suction, washed with THF and then dried. This gives a crude product yield of 28.8 g of light brown crystals. For further purification, these brownish crystals are heated with a solution of 100 ml of methanol/n-propanol (1:1) and 1 g of sodium hydroxide, the cloudy component is removed by filtration, the filtrate is cooled, and the precipitated white crystals are filtered off with suction and dried.

Yield: 22.4 g (≈75% of theory) of white crystals (m.p. 179–181° C.)

Static Heat Test

The mixtures in accordance with the following tables and their keys are each plasticated on a set of mixing rolls for 5 minutes at 180° C. or 190° C. Test strips are cut from the resultant films (thickness 0.3 mm) and these strips are subjected to thermal stress at 190° C. in a Mathis Thermo-Takter for the period indicated in the table below. Subsequently, the yellowness Index (YI) is determined in accordance with ASTM-1925-70. The lower the YI found, the more effective the stabilizer system.

Example I

The results are shown in Table 2 below. Low YI values denote good stabilization.

TABLE 2

| Minutes | Stabilizer Y 1.0 part | Stabilizer X 1.0 part | Stabilizer 4 1.0 part | Stabilizer 5 1.0 part | Stabilizer 6 1.0 part | Stabilizer 7 1.0 part |
|---|---|---|---|---|---|---|
| 0 | 6.51 | 8.97 | 5.21 | 7.80 | 6.45 | 16.63 |
| 5 | 10.53 | 8.54 | 6.36 | 8.56 | 6.91 | 17.90 |
| 10 | 13.60 | 10.57 | 6.57 | 10.53 | 8.04 | 19.56 |
| 15 | 16.13 | 17.95 | 7.77 | 15.77 | 10.33 | 26.86 |
| 20 | 19.48 | 33.66 | 11.87 | 26.40 | 16.78 | 33.77 |
| 25 | 27.60 | 56.48 | 20.31 | 38.46 | 23.25 | 42.20 |
| 30 | 39.21 | 81.72 | 29.04 | 47.74 | 31.05 | 54.37 |
| 35 | 54.71 | 105.68 | 39.77 | 56.58 | 42.02 | 68.32 |
| 40 | 76.35 | 139.31 | 49.35 | 66.77 | 55.96 | 82.80 |
| 45 | 110.41 |  | 60.62 | 76.65 | 70.17 | 95.13 |
| 50 |  |  | 73.23 | 89.19 | 81.50 | 108.46 |
| 55 |  |  | 90.08 | 109.57 | 97.91 | 122.64 |
| 60 |  |  | 122.89 | 150.67 | 138.35 |  |
| 65 |  |  |  |  |  |  |

TABLE 2-continued

| Minutes | Stabilizer 9 1.0 part | Stabilizer 10 1.0 part | Stabilizer 11 1.0 part | Stabilizer 14 1.0 part | Stabilizer 15 1.0 part | Stabilizer 18 1.0 part | Stabilizer 24 1.0 part |
|---|---|---|---|---|---|---|---|
| 0  | 4.86   | 5.04   | 7.87   | 5.31   | 5.56   | 5.25   | 7.90   |
| 5  | 5.77   | 5.46   | 12.68  | 7.47   | 7.80   | 5.22   | 8.20   |
| 10 | 5.80   | 6.18   | 16.48  | 10.47  | 9.95   | 6.46   | 9.60   |
| 15 | 7.79   | 8.06   | 20.48  | 17.82  | 13.79  | 10.96  | 14.57  |
| 20 | 12.41  | 10.66  | 23.76  | 32.87  | 20.34  | 16.47  | 25.00  |
| 25 | 17.88  | 18.72  | 28.60  | 56.95  | 30.02  | 25.47  | 41.13  |
| 30 | 21.75  | 26.37  | 35.27  | 88.40  | 42.91  | 42.82  | 60.48  |
| 35 | 33.85  | 33.70  | 45.74  | 129.81 | 56.78  | 58.84  | 78.90  |
| 40 | 47.14  | 42.55  | 56.03  |        | 77.14  | 80.58  | 95.20  |
| 45 | 46.30  | 54.05  | 66.44  |        | 112.10 | 109.38 | 117.48 |
| 50 | 53.82  | 66.04  | 78.98  |        |        | 166.31 | 140.61 |
| 55 | 65.25  | 78.36  | 111.01 |        |        |        |        |
| 60 | 81.64  | 99.83  |        |        |        |        |        |
| 65 | 113.59 | 147.98 |        |        |        |        |        |

Key to Table 2:

| | |
|---|---|
| 100.0 parts | Evipol SH 6030 = PVC K value 60 |
| 5.00 parts | ESO = epoxidized soybean oil |
| 0.40 part | Loxiol G 71 S = high molecular mass multicomponent ester = lubricant |
| 0.80 part | Irgastab CH 300 = liquid aryl dialkyl phosphite |
| 1.00 part | Stabilizer Y = 6-amino-1,3-dimethyluracil = prior art |
| 1.00 part | Stabilizer X = 6-phenylamino-1,3-dimethyluracil = prior art |
| 1.00 part | Stabilizer 4 = Example 4 |
| 1.00 part | Stabilizer 5 = Example 5 |
| 1.00 part | Stabilizer 6 = Example 6 |
| 1.00 part | Stabilizer 7 = Example 7 |
| 1.00 part | Stabilizer 9 = Example 9 |
| 1.00 part | Stabilizer 10 = Example 10 |
| 1.00 part | Stabilizer 11 = Example 11 |
| 1.00 part | Stabilizer 14 = Example 14 |
| 1.00 part | Stabilizer 15 = Example 15 |
| 1.00 part | Stabilizer 18 = Example 18 |
| 1.00 part | Stabilizer 24 = Example 24 |

Example II

The results are shown in Table 3 below. Low YI values denote good stabilization.

TABLE 3

| Minutes | Stabilizer X 0.2 part | Stabilizer 4 0.2 part |
|---|---|---|
| 0  | 54.36  | 20.00  |
| 5  | 58.17  | 21.64  |
| 10 | 57.13  | 21.93  |
| 15 | 57.22  | 22.65  |
| 20 | 65.53  | 26.50  |
| 25 | 73.97  | 33.69  |
| 30 | 82.25  | 46.86  |
| 35 | 92.55  | 68.41  |
| 40 | 112.65 | 92.12  |
| 45 | 132.01 | 115.15 |
| 50 |        | 131.68 |

Key to Table 3:

| | |
|---|---|
| 100.0 parts | Solvic 268 RC = PVC K value 68 |
| 3.0 parts | Omyalite 90 T = chalk |
| 0.6 part | Ca stearate |
| 1.0 part | Hostalub H 4 = modified hydrocarbon wax |
| 0.2 part | Hostalub H 12 = polar polyethylene wax |
| 1.0 part | Araldit GT 7220 = modified; solid bisphenol A epoxy resin |
| 0.4 part | Irgastab CH 302 = liquid aryl alkyl phosphite |
| 0.3 part | Mark 6045 = mixture of 9% NaClO$_4$, 45% CaCO$_3$, 40% CaSiO$_3$, 6% H$_2$O |
| 0.2 part | Stabilizer X = 6-phenylamino-1,3-dimethyluracil = prior art |
| 0.2 part | Stabilizer 4 = Example 4 |

The examples clearly show that the stabilizers of the invention give results not only in terms of initial color and color retention (middle color)—YI measurements—but also in terms of long-term stability—YI measurement—that are improved over the prior art.

What is claimed is:

1. A compound of the general formula I

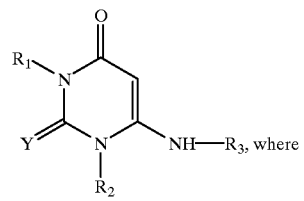

(I)

Y is oxygen or sulfur, and

R$_1$ and R$_2$ independently of one another are C$_1$–C$_{18}$-alkyl, C$_3$–C$_6$-alkenyl, unsubstituted or C$_1$–C$_4$-alkoxy-, $C_5$–$C_8$-cycloalkyl-, —OH— and/or Cl-substituted $C_1$–$C_{18}$-alkyl, $C_5$–$C_8$-cycloalkyl, phenyl or $C_7$–$C_9$-phenylalkyl which is unsubstituted or substituted on the phenyl ring by $C_1$–$C_4$-alkyl, $C_1$–$C_4$-alkoxy, $C_5$–$C_8$-cycloalkyl, —OH and/or Cl, and $R_3$ is unsubstituted $C_9$–$C_{18}$-alkyl or is $C_1$–$C_{18}$-alkyl substituted up to 5 times by —OH, $C_1$–$C_{12}$-alkoxy, phenoxy, $C_6$–$C_8$-alkylphenoxy, $C_7$–$C_9$-alkoxyphenyl, —C=O(OR$_4$) and/or —O—COR$_4$, or is $C_3$–$C_6$-alkenyl, $C_5$–$C_8$-cycloalkyl, or mono- to tri-OH—, —$C_1$–$C_4$-alkyl-, —$C_1$–$C_4$-alkoxy-, —C=O(OR$_4$)— and/or —O—COR$_4$-substituted phenyl or naphthyl, and where $R_4$ is $C_1$–$C_{12}$-alkyl.

2. A compound as claimed in claim 1, where

Y is oxygen.

3. A compound as claimed in claim 1, where $R_1$ and $R_2$ independently of one another are $C_1$–$C_8$-alkyl, allyl or $C_7$–$C_9$-phenylalkyl.

4. A compound as claimed in claim 1, where $R_3$ is $C_9$–$C_{18}$-alkyl or —OH-substituted $C_1$–$C_{12}$-alkyl, cyclohexyl, allyl, $C_7$–$C_9$-phenylalkyl or —OH—, $C_1$–$C_4$-alkyl-, $C_1$–$C_4$-alkoxy-, —C=O(OR$_4$)— and/or —O—COR$_4$-substituted phenyl or naphthyl.

5. A compound as claimed in claim 1 where $R_1$ and $R_2$ are $C_1$–$C_4$-alkyl, and $R_3$ is —OH-substituted $C_1$–$C_4$-alkyl, benzyl, phenyl, —OH-substituted phenyl or phenyl which is substituted by —OH and from 1 to 3 times by $C_1$–$C_4$-alkyl.

6. A composition comprising a chlorine-containing polymer and at least one compound of the general formula I as claimed in claim 1.

7. A composition as claimed in claim 6 comprising at least one epoxidized fatty acid ester.

8. A composition as claimed in claim 6 comprising at least one zinc carboxylate and/or alkali metal carboxylate and/or alkaline earth metal carboxylate and/or aluminum carboxylate.

9. A composition as claimed in claim 6 comprising at least one further substance from the groups of the phosphites, antioxidants, beta-dicarbonyl compounds, plasticizers, fillers, lubricants or pigments.

10. A composition as claimed in claim 6 comprising chalk as filler.

11. A composition as claimed in claim 6 comprising calcium stearate as lubricant.

12. A composition as claimed in claim 6 comprising titanium dioxide and/or zirconium oxide and/or barium sulfate as pigment.

13. A composition as claimed in claim 6 comprising at least one polyol and/or a disaccharide alcohol.

14. A composition as claimed in claim 6 comprising at least one glycidyl compound.

15. A composition as claimed in claim 6 comprising at least one perchlorate compound.

16. A composition as claimed in claim 6 comprising at least one zeolite compound.

17. A composition as claimed in claim 6 comprising at least one layered lattice compound (hydrotalcites).

18. A composition as claimed in claim 6 comprising at least one hydrotalcite.

19. A method of stabilizing chlorine-containing polymers which comprises incorporating into said polymers at least one compound of the formula I as claimed in claim 1.

20. A method for stabilizing a halogen-containing polymer which comprises adding a stabilizing effective amount of at least one compound of claim 1 to a halogen-containing polymer.

21. The method of claim 20 wherein said halogen-containing polymer is a recycled halogen-containing polymer.

22. The composition of claim 1 wherein Y is oxygen and $R_1$ and $R_2$ are each methyl.

23. The composition of claim 22 wherein $R_3$ is 2-hydroxyphenyl, 2-hydroxy-4-methylphenyl or 2-hydroxy-5-t-butylphenyl.

24. The composition of claim 1 wherein Y is oxygen, $R_1$ and $R_2$ are each n-butyl, and $R_3$ is 2-hydroxyphenyl.

* * * * *